United States Patent
Yi et al.

(10) Patent No.: US 11,161,958 B2
(45) Date of Patent: Nov. 2, 2021

(54) MACROPOROUS CHITOSAN-POLYACRYLAMIDE HYDROGEL MICROSPHERES AND PREPARATION THEREOF

(71) Applicant: Trustees of Tufts College, Medford, MA (US)

(72) Inventors: Hyunmin Yi, Lexington, MA (US); Sukwon Jung, Gyeyang-gu (KR); John H. Abel, Medford, MA (US)

(73) Assignee: Trustees of Tufts College, Medford, MA (US)

(*) Notice: Subject to any disclaimer, the term of this patent is extended or adjusted under 35 U.S.C. 154(b) by 65 days.

(21) Appl. No.: 16/311,063

(22) PCT Filed: Jun. 22, 2017

(86) PCT No.: PCT/US2017/038755
§ 371 (c)(1),
(2) Date: Dec. 18, 2018

(87) PCT Pub. No.: WO2017/223315
PCT Pub. Date: Dec. 28, 2017

(65) Prior Publication Data
US 2019/0263999 A1 Aug. 29, 2019

Related U.S. Application Data

(60) Provisional application No. 62/353,273, filed on Jun. 22, 2016.

(51) Int. Cl.
*C08J 9/28* (2006.01)
*C08F 2/46* (2006.01)
(Continued)

(52) U.S. Cl.
CPC ............. *C08J 9/286* (2013.01); *A61K 9/1635* (2013.01); *A61K 9/1641* (2013.01);
(Continued)

(58) Field of Classification Search
CPC .................................. C08L 33/26; C08L 5/08
See application file for complete search history.

(56) References Cited

U.S. PATENT DOCUMENTS

2006/0210710 A1   9/2006 Buiser et al.
2008/0102276 A1*  5/2008 Khademhosseini .... A61L 27/52
                                                              428/403

(Continued)

FOREIGN PATENT DOCUMENTS

FR      2785811 A1 *  5/2000  ............. A61L 27/52

OTHER PUBLICATIONS

Dragan et al. Chemical Engineering Journal 204-206 (2012) 198-209. Macroporous composite IPN hydrogels based on poly(acrylamide) and chitosan with tuned swelling and sorption of cationic dyes. (Year: 2012).*

(Continued)

*Primary Examiner* — Michael M Dollinger
(74) *Attorney, Agent, or Firm* — Dana M. Gordon; Foley Hoag LLP (57) ABSTRACT

Disclosed is a macroporous polymeric hydrogel microsphere that contains polyacrylamide and chitosan. The hydrogel microsphere, having a diameter of 50-250 μm and an average pore size of 1-60 nm, is capable of transporting biomolecules conjugated to it. Also disclosed is a method of fabricating the microsphere based on a micromolding technique utilizing surface tension-induced droplet formation followed by photo-induced polymerization.

17 Claims, 5 Drawing Sheets

(51) Int. Cl.
*C08F 20/56* (2006.01)
*C08J 3/075* (2006.01)
*C08F 220/56* (2006.01)
*C08L 33/26* (2006.01)
*A61K 9/16* (2006.01)

(52) U.S. Cl.
CPC .............. *A61K 9/1652* (2013.01); *C08F 2/46* (2013.01); *C08F 20/56* (2013.01); *C08F 220/56* (2013.01); *C08J 3/075* (2013.01); *C08L 33/26* (2013.01); *C08F 2800/20* (2013.01); *C08J 2205/022* (2013.01); *C08J 2305/08* (2013.01); *C08J 2333/26* (2013.01); *C08J 2471/00* (2013.01)

(56) References Cited

U.S. PATENT DOCUMENTS

| | | | |
|---|---|---|---|
| 2010/0291055 A1* | 11/2010 | Athanasiadis | A61L 31/041 424/94.1 |
| 2011/0104052 A1 | 5/2011 | Barnett et al. | |
| 2012/0058355 A1* | 3/2012 | Lee | G02B 27/0006 428/515 |
| 2014/0370500 A1 | 12/2014 | Ghanavi et al. | |
| 2015/0114580 A1* | 4/2015 | McKee | C08B 31/006 162/123 |
| 2015/0217024 A1* | 8/2015 | Wang | A61L 27/3817 424/400 |
| 2016/0271064 A1* | 9/2016 | Sell | A61K 9/1682 |
| 2016/0319059 A1* | 11/2016 | Vlasov | A61L 27/54 |
| 2019/0111412 A1 | 4/2019 | Yi et al. | |

OTHER PUBLICATIONS

Zhao et al. Composites: Part B 43 (2012) 1570-15781571. Removal of anionic dyes from aqueous solutions by adsorption of chitosan-based semi-IPN hydrogel composites. (Year: 2012).*
Chirani et al., "History and Applications of Hydrogels," Journal of Biomedical Science, 4(2):Abstract (2015).
Database Pubchem, "Hexadecane", XP055449835, Database accession No. CID 11006, Sep. 16, 2004 (Sep. 16, 2004).
Gupta et al., "How Relative Humidity Affects Evaporation," p. 1 (2011).
Hiratsuka et al., "Water Droplet Lubrication Between Hydrophilic and Hydrophobic Surfaces," Jounral of Physics, 89:2 (2007).
International Search Report and Written Opinion for International Application No. PCT/US17/38755 dated Sep. 25, 2017.
Mane et al., "Effect of porogens (type and amount) on polymer porosity: a review," Can Chem Trans, 4(2):210-225 (2016).
International Preliminary Report on Patentability for International Application No. PCT/US2017/038755 dated Dec. 25, 2018.

* cited by examiner

MACROPOROUS CHITOSAN-POLYACRYLAMIDE HYDROGEL MICROSPHERES AND PREPARATION THEREOF

CROSS REFERENCE TO RELATED APPLICATIONS

This application is the National Stage of International Application No. PCT/US2017/038755, filed on Jun. 22, 2017; which claims the benefit of US Provisional Application No. 62/353,273, filed on Jun. 22, 2016.

BACKGROUND

Hydrogel microparticles have a wide range of applications, including catalysis, drug delivery, and bio-sensing. In particular, they have gained increasing attention for their use as bio-sensing platforms in diagnosis and biological threat detection.

Specific performance of hydrogel microparticles can be achieved by controlling their morphology, mesh size, and other structural features.

When fabricated via batch processes using dispersion or emulsion polymerization, hydrogel microparticles are generally polydisperse, i.e., non-uniform. Microfluidics-based techniques have been employed to fabricate highly uniform hydrogel microspheres. Yet, this approach requires complex devices and is not scalable.

Polymerization-induced phase separation has been developed using poly(ethylene glycol) diacrylate as the polymerizable monomer to control the pore size of hydrogel microparticles. However, it still limits the pore size and thus mass transfer of biomolecules.

Various porogens have been used in fabricating hydrogel microparticles. However, their use often leads to non-uniform network structures and compromised mechanical integrity.

There is a need to develop facile fabrication of desirable macroporous hydrogel microspheres.

SUMMARY

The present invention relates to a process of preparing polymeric hydrogel microspheres containing macropores. Unexpectedly, this process allows for facile fabrication of monodisperse (i.e., uniform) hydrogel microspheres with controlled macroporous structures. Further, the hydrogel microspheres thusly prepared exhibit an unexpectedly high protein conjugation capacity.

In one aspect, this invention is a method of fabricating a polymeric hydrogel microsphere. The method includes steps: (1) providing an aqueous pre-polymer solution containing acrylamide, bisacrylamide, and chitosan, the total content of acrylamide and bisacrylamide being 5-50 w/v %; (2) filling an elastomeric poly-dimethylsiloxane micromold with the aqueous pre-polymer solution; (3) adding a hydrophobic wetting fluid containing a photo-initiator onto the filled micromold; (4) inducing formation of a droplet via surface tension; (5) exposing the droplet to UV light to crosslink the pre-polymer solution; and (6) collecting the thus-formed microsphere.

These steps are performed in series. Steps (1)-(3) are preferably conducted in a humid chamber with a humidity of 90-98% (e.g., 94%).

In one embodiment, the aqueous pre-polymer solution is formed of acrylamide and bisacrylamide, in which the content of bisacrylamide is 0.25-25 w/w % (e.g., 0.25-10 w/w % and 0.25-5 w/w %) as compared to the total amount of acrylamide and bisacrylamide. A poly(ethylene glycol) porogen, having a molecular weight of 200 to 20,000 Da (e.g., 7,000-9,000 Da), can be added into the aqueous pre-polymer solution provided in step (1). Typically, this porogen has a content of 10 w/v % or lower (e.g., 1-7.5 w/v %, 2.5-5 w/v %, and 5-10 w/v %).

The elastomeric poly-dimethylsiloxane micromold used in step (2) has various geometries (e.g., cross-shaped, triangle, square, circle, pentagon, or hexagon) and also has various sizes (e.g., 1-10 nL).

Turning to step (3), n-hexadecane, can be used as the solvent to prepare the hydrophobic wetting fluid, and 2-hydroxy-2-methylpropiophenone can be used as the photo-initiator.

In one embodiment of the method set forth above, the content of bisacrylamide is 0.25-5 w/w % as compared to the total content of acrylamide and bisacrylamide, the hydrophobic wetting fluid is formed of 2-hydroxy-2-methylpropiophenone and n-hexadecane, and the providing, filling, and adding steps are conducted in a humid chamber with a humidity of 90-98%.

The method of this invention can further include a step of sequentially washing the collected microsphere with 2-propanol, de-ionized water, and a saline sodium citrate buffer solution.

Another aspect of this invention is a macroporous polymeric hydrogel microsphere that can be prepared by the above-described method.

The macroporous polymeric hydrogel microsphere contains chitosan and polyacrylamide, in which the chitosan is uniformly incorporated in a matrix formed of the polyacrylamide. The hydrogel microsphere typically has a diameter of 50-250 μm and an average pore size of 1-60 nm. Preferably, it has a diameter of 150-250 μm, and more preferably, 200-240 μm (e.g., 227 μm). Preferred and more preferred pore sizes are 10-60 nm and 30-60 nm (e.g., 39 nm), respectively.

Chitosan is known to contain primary amines having a pKa value of 6.0-6.9 (e.g., 6.4). The chitosan in the hydrogel microsphere of this invention typically has an average molar mass of 4,000-6,000 Da (e.g., 5,000 Da). It can also be a long chain chitosan that has an average molar mass of 100,000-1,000,000 Da (e.g., 200,000 Da).

Further, the hydrogel microsphere can have an anisotropic network structure. Of note, the chitosan in the hydrogel microsphere contains primary amines, which are capable of conjugating with biomolecules via substitution nucleophilic $S_N2$ reaction.

Typically, the hydrogel microsphere is capable of conjugating to a biomolecule that has a molecular weight of 10,000-300,000 Da (e.g., 20,000-300,000 Da).

The details of the invention are set forth in the description below. Other features, objects, and advantages of the invention will be apparent from the following drawings and detailed description of several embodiments, and also from the appending claims.

BRIEF DESCRIPTION OF THE DRAWINGS

(b): A micrograph of CS—PAAm microspheres in aqueous solutions and their size distribution. (c): Micrographs of CS—PAAm microspheres prepared with prepolymer solutions containing various monomer compositions (each scale bar representing 200 μm). (d): Micrographs of CS—PAAm microspheres prepared with prepolymer solutions containing poly(ethylene glycol) (PEG) 8kDa porogen at various contents (each scale bar representing 200 μm). (e): A brightness plot for microspheres with increased PEG porogen contents (circles) and for background brightness (squares), each error bar representing the standard deviation of five microspheres and five backgrounds under each condition.

FIG. 2 is a schematic depiction of fluorescent labeling of CS—PAAm microspheres. (a): Fluorescent labeling of CS—PAAm microspheres via amidation reaction. (b)-(d): Fluorescence micrographs of CS—PAAm microspheres prepared with PEG porogen at various contents and a fixed amount of chitosan upon fluorescent labeling (each scale bar representing 200 μm). (e)-(g): Fluorescence micrographs of negative control microspheres without chitosan upon incubation with 5- or 6-carboxyfluorescein succinimidyl ester (each scale bar representing 200 μm), the insets being bright-field micrographs corresponding to the fluorescence micrographs of the negative controls. (h): A total fluorescence intensity plot for fluorescein-labeled microspheres measured immediately (white columns) and upon 3-month storage in a buffer solution (gray columns), each error bar representing the standard deviation of five microspheres under each condition.

FIG. 4 is a schematic depiction of the effect of PEG porogen on protein conjugation kinetics. (a)-(c): Total fluorescence intensity plots of CS—PAAm microspheres prepared with various PEG porogen contents (1.5-5%) upon R-PE conjugation for various reaction times (0-48 h) (each scale bar representing 200 μm and each error bar representing the standard deviation of five microspheres under each condition), the insets being confocal micrographs of the R-PE conjugated microspheres at the middle plane upon 1 h, 24 h, and 48 h-conjugation reactions.

FIG. 5 are schematic comparisons between measured and estimated R-PE concentration distributions for CS—PAAm microspheres. (a): Normalized fluorescence intensity plots (circles and squares) measured from the confocal micrographs shown in FIG. 4 and normalized R-PE concentration distribution plots (solid and dashed curves) estimated with the equation describing non-steady state solute diffusion in a sphere at 1 h transient time. (b): Normalized fluorescence intensity plots as in (a) except that the transient time was 24 h.

DETAILED DESCRIPTION

Within this invention is a method of preparing macroporous chitosan-polyacrylamide hydrogel microspheres based on a micromolding technique utilizing surface tension-induced droplet formation followed by photo-induced polymerization. Hydrogels, i.e., crosslinked hydrophilic polymers, have emerged as an important class of materials for a wide range of applications in catalysis, medicine, and bio-sensing. In particular, suspension arrays of bio-functionalized hydrogel particles with dimensions in the micrometer ranges provide significant utility as bio-sensing platforms in medical diagnostics and biological threat detection due to several inherent advantages over planar arrays. These advantages include rapid solution-like binding kinetics and short assay time, small sample volume, and favorable interactions between the probes and targets in hydrophilic environments. Recent advances in lithographic fabrication techniques (e.g., photolithography and stop-flow lithography) have enabled rapid or high-throughput sensing of biomacromolecular targets such as nucleic acids and proteins through traits including controlled structures and dimensions, multiple discrete compartments for multiplexed assays, as well as complex shapes allowing for potent encoding. Despite these advances, it remains challenging for current fabrication techniques to satisfy multiple criteria for rapid and robust bioassay platforms and other biological applications. Outstanding barriers to efficient bioassay development include limited choice of polymeric matrix materials, requirement of complex equipment and delicate flow control, slow and hindered mass transfer of biomacromolecular targets through the particles, potential damage to biomolecular probes in commonly enlisted co-polymerization schemes, and difficulty in cost-efficient scale-up.

Most techniques for fabricating hydrogel particles utilize poly(ethylene glycol) diacrylate (PEGDA) as the polymerizable monomer, given its rapid polymerization rate and the nonfouling nature of the resulting poly(ethylene glycol) (PEG) polymer chains. Success has been achieved in tuning the mesh size of the crosslinked PEG chains with inert short chain PEG porogens for improved mass transfer of large biomolecular target and in controlling mesh sizes via polymerization-induced phase separation. See Duenas et al., *Biotechnol. Bioprocess Eng.*, 2015, 20, 956-964; and Jung et al., *Chem. Mater.*, 2015, 27, 3988-3998. Yet, the inherent crosslinking nature of PEGDA still limits the mesh size and the mass transfer of large biomolecules through the polymeric networks. There remains a need to overcome challenges of developing simple, low-cost, and readily scalable methods for fabricating hydrogel microparticles with controlled and large mesh sizes that permit rapid mass transfer of biomacromolecules in a short assay time.

To meet this need, a new method is disclosed herein for fabricating a polymeric hydrogel microsphere. The method is performed by conducting the following steps in series. First, an aqueous pre-polymer solution containing acrylamide, bisacrylamide, and chitosan is prepared, in which the total content of acrylamide and bisacrylamide is 5-50 w/v %; second, the aqueous pre-polymer solution is filled in an elastomeric poly-dimethylsiloxane micromold; third, a hydrophobic wetting fluid containing a photo-initiator is added onto the filled micromold; fourth, formation of a droplet is induced via surface tension; fifth, the droplet is exposed to UV light to crosslink the pre-polymer solution; and finally, a polymeric hydrogel microsphere is then formed and collected.

Typically, the first three steps are conducted in a humid chamber with a pre-determined humidity, e.g., 90-98% and 94%. is As pointed out above, the aqueous pre-polymer solution contains acrylamide, bisacrylamide, and chitosan. Based on the total amount of acrylamide and bisacrylamide, the content of bisacrylamide can be 0.25-25 w/w %, preferably 0.25-10 w/w %, or most preferably 0.25-5 w/w %. The chitosan, which contains primary amines having a pKa value of 6.0-6.9 (e.g., 6.4), typically has an average molar mass of 4,000-6,000 Da, preferably about 5,000 Da. It can also be a long chain chitosan that has an average molar mass of 100,000-1,000,000 Da, preferably about 200,000 Da.

In one embodiment, a poly(ethylene glycol) porogen is added into the aqueous pre-polymer solution described above. Typically, the porogen has a molecular weight of 200 to 20,000 Da, or preferably, 7,000-9,000 Da. It can be present at a content of 10 w/v % or lower. In an exemplary method, a porogen is present at a content of 1-7.5 w/v %, 2.5-5 w/v %, or 5-10 w/v %.

As pointed out above, the elastomeric poly-dimethylsiloxane micromold used in this method can have various geometries (e.g., cross-shaped, triangle, square, circle, pentagon, and hexagon) and also can have various sizes (e.g., 1-10 nL).

Also within the scope of this invention is a macroporous polymeric hydrogel microsphere prepared by the above-described method.

To reiterate, the macroporous polymeric hydrogel microsphere thus prepared contains chitosan (CS) and polyacrylamide (PAAm), in which the chitosan is uniformly incorporated in a matrix formed of polyacrylamide. In general, the hydrogel microsphere has a diameter of 50-250 µm (e.g., 150-250 µm, 200-240 µm, and 227 µm) and an average pore size of 1-60 nm (e.g., 10-60 nm, 30-60 nm, and 39 nm).

An exemplary hydrogel microsphere of this invention, having an anisotropic network structure, is capable of conjugating to a biomolecule that has a molecular weight of 10,000-300,000 Da (e.g., 20,000-300,000 Da).

In sum, a simple and robust micromolding-based method has been developed to prepare monodisperse CS—PAAm microspheres. Advantages of this method include: (i) a wide range of parameters can be readily modulated to confer suitable properties (e.g., large mesh size) of the microspheres thus obtained; (ii) addition of chitosan in an aqueous pre-polymer mixture leads to stable incorporation, imparting efficient chemical conjugation due to the highly nucleophilic nature of its primary amines (arising from the low $pK_a$ value of about 6.4) at nearly every glucosamine monomer unit; (iii) addition of a low content (<2.5 w/v %) long chain (LC) PEG porogen (8 kDa) leads to macroporous polymer networks, substantially improving the protein conjugation kinetics and the capacity; (iv) as demonstrated in all fluorescent labeling and protein conjugation studies performed, the CS—PAAm microspheres have minimal non-specific binding or non-fouling for hydrophobic dyes and proteins; and (v) in-depth protein conjugation studies via rapid tetrazine-trans-cyclooctene (Tz-TCO) reaction and confocal microscopy reveal both improved protein conjugation kinetics by simple addition of LC PEG porogens, indicating increase in mesh size, and anisotropic polymer network structures of the microspheres suitable for differential biofunctionalization schemes.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All of the publications cited herein are incorporated by reference.

Provided below are materials used in fabricating macroporous chitosan-polyacrylamide hydrogel microspheres of this invention and methods for analyzing the microspheres thus prepared.

Materials and Methods

1. Materials

Chitosan oligosaccharide lactate (average $M_n$ 5 kDa, >90% deacetylation), acrylamide, bis-acrylamide (N,N'-methylenebisacrylamide, Bis), poly(ethylene glycol) (PEG, average M. W. 8 kDa), 2-hydroxy-2-methylpropiophenone (photoinitiator, as known as Darocur 1173), phosphate buffered saline (PBS) tablets (10 mM phosphate, 2.7 mM potassium chloride, 137 mM sodium chloride, pH 7.4), and saline sodium citrate (SSC) buffer (20× concentrate, molecular biology grade) were purchased from Sigma-Aldrich (St. Louis, Mo.). 5- and 6-carboxyfluorescein succinimidyl ester (NHS-fluorescein) were purchased from Pierce Biotechnology (Rockford, Ill). Trans-cyclooctene (TCO)-$PEG_4$-N-hydroxysuccinimide (NHS) ester and Tetrazine (Tz)-$PEG_5$-NHS ester were purchased from Click Chemistry Tools (Scottsdale, Ariz.). Borate buffer (20× concentrate, 50 mM borate, pH 8.5), Tween 20 (TW20) and poly(dimethylsiloxane) (PDMS) elastomer kits (Sylgard 184, Dow Corning, Auburn, MI) and centrifugal filter units (Amicon® Ultra 0.5 ml, EMD Millipore) were purchased from Thermo Fisher Scientific. N-hexadecane (99%) and 2-propanol (>99.7%) were purchased from ACROS Organics™ and J.T.Baker®, respectively. Red fluorescent protein R-Phycoerythrin (R-PE in sodium phosphate buffer, pH 7.0 with ammonium sulfate) was purchased from AnaSpec (Fremont, Calif.). All the chemicals were analytical grade, and used without further purification.

2. Fabrication of Chitosan-Polyacrylamide Microspheres

As shown in FIG. 1a, chitosan-polyacrylamide (CS—PAAm) microspheres were fabricated via a simple micromolding-based approach as reported in Jung et al., *Chem. Mater.*, 2015, 27, 3988-3998.

More specifically, a PDMS mold consisting of cross-shaped microwells was prepared via overnight thermal curing (65° C.) of Sylgard 184 elastomer on a photolithographically patterned silicon master mold. Aqueous prepolymer solutions were prepared by mixing monomers (acrylamide and Bis), PEG 8 kDa, chitosan and deionized (DI) water. The composition of the prepolymer solution was as follows: 5-15 w/v % monomer (0.25-25 w/w % Bis over acrylamide), 0-10 w/v % PEG 8 kDa, and 0.5 w/v % chitosan. Hydrophobic wetting fluid was prepared by mixing N-hexadecane and photoinitiator (1 v/v %). The prepolymer solution was placed on the PDMS mold, and filled into the microwells by rubbing the mold with a disposable pipet tip. The excess prepolymer solution was removed by pipetting, and the wetting fluid (100 µl) was placed on the filled mold. To prevent rapid evaporation of water in the prepolymer solution, these procedures were carried out in a humidity chamber (about 94% humidity). The mold was subsequently taken out of the humidity chamber and left on an aluminum mirror (Thorlabs, Newton, N.J.) for at least 2 minutes for droplet formation by surface tension between the hydrophilic prepolymer solution and the hydrophobic wetting fluid. 365 nm UV light was then exposed to the droplets thus formed for 1 h with an 8 W hand-held UV lamp (Spectronics Corp., Westbury, N.Y.) to crosslink the individual droplets. The crosslinked droplets were then collected in a microcentrifuge tube and sequentially washed with 2-propanol (5 times), DI water containing 0.5% (v/v) TW20 (3 times), and 5x SSC buffer solution containing 0.05% (v/v) TW20 (SSC-TW20 buffer solution, 2 times).

3. Fluorescent Labeling of CS—PAAm Microspheres

For fluorescent labeling, the as-prepared CS—PAAm microspheres (about 50 particles) were incubated in SSC-TW20 buffer solution containing 100 µM of NHS-fluorescein for 1 h at room temperature on a rotator covered with aluminum foil to minimize light exposure. The microspheres were then washed 5 times with 50% (v/v) 2-propanol aqueous solution to remove unreacted fluorescein molecules.

4. Modification of Proteins with TCO

To prepare TCO-modified R-PEs, a buffer solution of the R-PE was exchanged with borate buffered saline (50 mM borate, 300 mM NaCl, pH 8.5) via centrifugal filtration (Amicon Ultra 0.5) at 4° C. 2 mg/mL of the R-PEs were then reacted with 20-fold molar excess of TCO-PEG$_4$-NHS ester for 30 min at room temperature, and the TCO-modified R-PEs were purified from unreacted residues via centrifugal filtration with PBS buffer solution (pH 7.4). Concentration of the final R-PE solution was measured by UV-vis spectrophotometry (Evolution™ 300 UV-vis Spectrophotometer, Thermo scientific, Waltham, Mass.) with the characteristic absorbance peak and molar extinction coefficient of the R-PE ($1.96 \times 10^6$ $M^{-1}cm^{-1}$ at 565 nm).

5. Protein Conjugation with CS—PAAm Microspheres

Tz-TCO ligation reaction was performed to conjugate the R-PEs with the CS—PAAM microspheres thus obtained. The CS—PAAM microspheres were first activated with Tz molecules by incubating them in SSC-TW20 buffer solution containing 500 µM of Tz-PEG$_5$-NHS ester for 1 h at room temperature. After washed 5 times the microspheres with a SSC-TW20 buffer solution, the Tz-activated microspheres (about 50 microspheres) were reacted with 2 µM of the TCO-modified R-PEs in SSC-TW20 buffer solution for varying reaction times (0-48 h) at room temperature. The microspheres were purified from unconjugated R-PEs by washing them 5 times with the SSC-TW20 buffer solution.

6. Imaging Analysis

The fluorescently labeled and R-PE conjugated microspheres were imaged with an epifluorescence microscope (Olympus BX51 equipped with a DP70 microscope digital camera, Center Valley, Pa.) and a confocal microscope (Leica DMIRE2 equipped with a TCS SP2 scanner, Wetzlar, Germany) in SSC-TW20 buffer solution. Epifluorescence micrographs of the fluorescently labeled and R-PE conjugated microspheres were obtained with a 10× objective lens under standard green (U-N31001) and red (U-N31002) filter sets (Chroma Technology Corp., Rockingham, Vt.), respectively. Confocal micrographs of the fluorescently labeled and R-PE conjugated microspheres were obtained with a 20× objective lens under 488 nm and 543 nm excitation, respectively, and the depth scan increment was 5 µm. Diameters and fluorescence intensities of the microspheres were analyzed with the image analysis software ImageJ.

7. Mass Transfer Analysis

In order to analyze mass transfer of the R-PEs through microspheres shown in FIGS. 4a and 4b, diffusion coefficients of the R-PEs in microspheres were calculated with varying pore sizes ($D_m$) by utilizing Renkin equation (1) shown below:

$$\frac{D_m}{D_0} = \left(1 - \frac{d_h}{d_p}\right)^2 \times \left[1 - 2.10\left(\frac{d_h}{d_p}\right) + 2.09\left(\frac{d_h}{d_p}\right)^2 - 0.95\left(\frac{d_h}{d_p}\right)^5\right] \quad (1)$$

where $d_h$ and $d_p$ represent hydrodynamic diameter of the R-PE (11.2 nm) and pore diameter of microspheres, respectively. $D_0$ represents a diffusion coefficient of the R-PE in bulk solution that can be calculated according to Stokes-Einstein equation (2):

$$D_0 = \frac{k_B T}{3\pi \eta d_h} \quad (2)$$

where T and η represent temperature and viscosity of solution, respectively, and $k_B$ is Boltzmann constant ($1.38 \times 10^{-23}$ $J \cdot K^{-1}$).

Assuming diffusion-limited mass transfer of the R-PE in a conjugation system, diffusion profiles (i.e., concentration distributions) of the R-PE in the microspheres, which possess varying pore diameters at transient time, were calculated by utilizing the estimated diffusion coefficients ($D_m$) and the following non-steady state diffusion equation (3) in a sphere:

$$\frac{C}{C_0} = 1 + \frac{2R}{\pi r}\sum_{n=1}^{\infty}\frac{(-1)^n}{n}\sin\frac{n\pi r}{R}e^{-(D_m n^2 \pi^2 t/R^2)} \quad (3)$$

where C represents concentration of the R-PE at a location in a sphere (r) and transient time (t). $C_0$ represents constant concentration of the R-PE at the sphere surface (assumed as 2 µM), and R is radius of microspheres (136 µm). The estimated diffusion profiles were then directly compared to normalized fluorescence profiles measured from the confocal micrographs at the center plane of the micro spheres that are shown in FIGS. 4a and 4b.

EXAMPLE 1

Fabrication of CS—PAAm Microspheres with Varying Prepolymer Compositions

Several CS—PAAm hydrogel microspheres with varying prepolymer compositions were prepared and characterized as follows.

Figure 1:
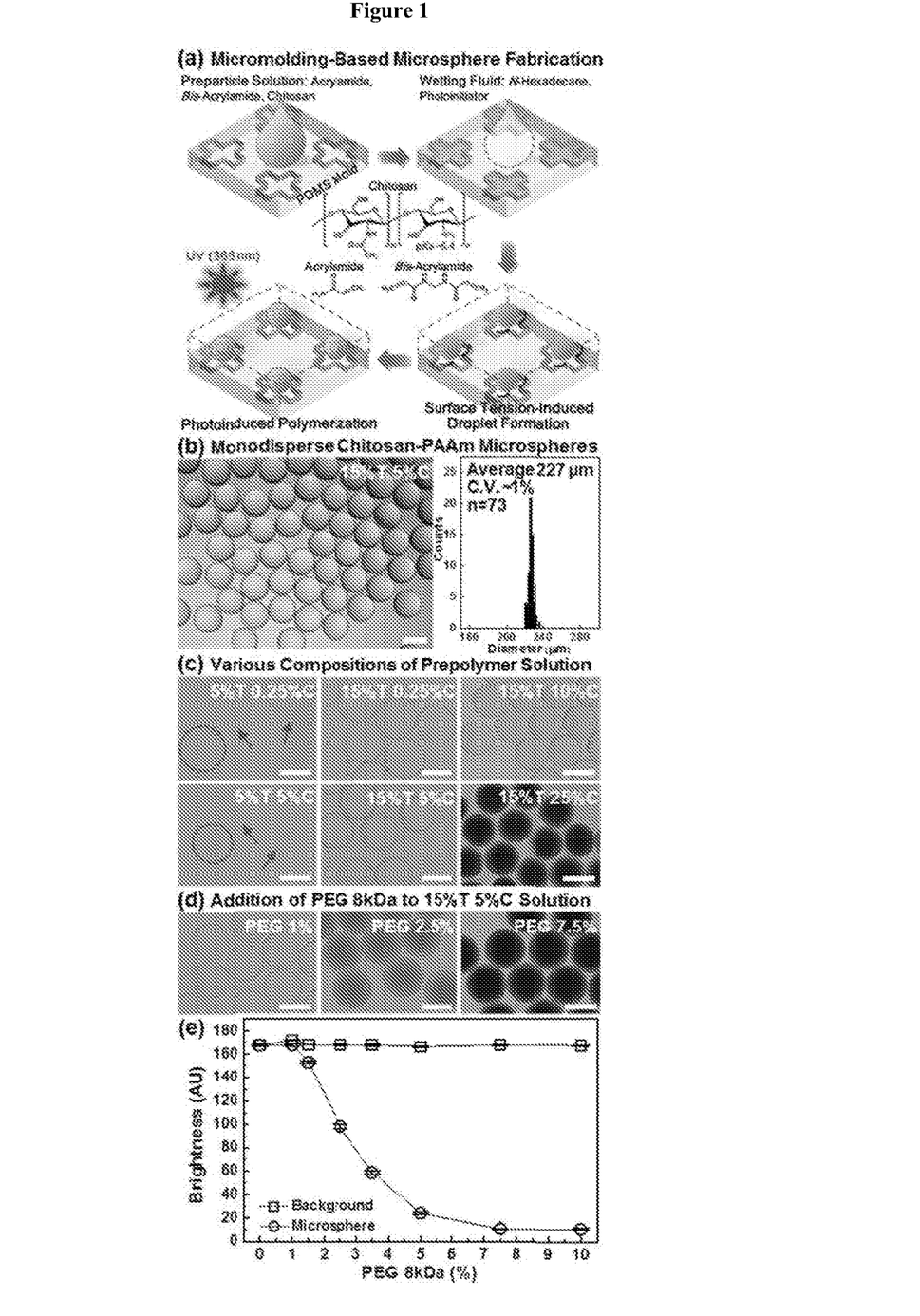
FIG. 1 is a schematic depiction of fabricating chitosan-polyacrylamide (CS-PAAm) microspheres using a micro-molding-based technique. (a): A procedure of microsphere fabrication and the chemical structures of chitosan, acrylamide, and bis-acrylamide.

FIG. 1 shows that a simple and robust micromolding-based fabrication provided monodisperse microspheres with controlled macroporous structures containing biopolymeric-synthetic hybrid polymer hydrogels.

The fabrication procedure shown in FIG. 1a started with filling cross-shaped poly(dimethylsiloxane) (PDMS) microwells with simple aqueous mixtures (i.e., prepolymer solutions) of short-chain chitosan ($M_n$ 5 kDa, 0.5 w/v %) and varying contents of acrylamide and Bis as the polymerizable monomers. Upon covering the prepolymer-filled microwell patterns with hydrophobic wetting fluid N-hexadecane containing 1 v/v % of photoinitiator (PI), the surface tension-induced pressure triggered the hydrophilic prepolymer solutions to be pushed out of the microwells and to form uniform spherical droplets. These droplets were then cured with a simple hand held UV lamp (365 nm, 8 W) to form cross-linked hydrogel microspheres via UV-induced radical polymerization. This simple fabrication scheme led to highly uniform microspheres, as shown in the bright-field micrograph and particle size distribution of a representative batch in FIG. 1b (i.e., coefficient of variation or CV of about 1% for n=73).

As shown in FIGS. 1c and 1d, a range of monomer compositions were examined for fabrication of CS—PAAm microspheres. Prepolymer solutions were prepared by simply mixing in water a fixed content of chitosan and various total monomer concentrations (%T, total monomer weight (acrylamide and Bis) per total volume in g/100 mL) with various Bis ratios (%C, weight of Bis per total monomer weight), i.e., 5%T with 0.25%C, 5%T with 5%C, 15%T with 0.25%C, 15%T with 5%C, 15%T with 10%C, and 15%T with 25%C. The solutions thus prepared were added to cross-shaped PDMS micromolds then covered with the wetting fluid N-hexadecane containing PI, and the resulting droplets were cured with a UV lamp as shown in the schematic diagram of FIG. 1a.

The bright-field micrographs in FIG. 1c show that CS—PAAm microspheres were readily fabricated with low monomer content (5-15%T) in a reliable and consistent manner via the micromolding method described above. CS—PAAm microspheres with prepolymer solutions containing higher monomer content (>15%T) were also readily fabricated in a reliable manner (data not shown), while the mesh size of PAAm networks for such microspheres decreased with increasing monomer contents, leading to diffusion limitation of large biomolecules through the microspheres. See FIG. 3b below. Meanwhile, the bright-field micrographs of 5%T conditions show nearly transparent CS—PAAm microspheres (marked with dashed lines and arrows in the leftmost column) compared to the 15%T microspheres (middle column). In addition, the sizes of 5%T microspheres were larger than those of 15%T ones in the aqueous environment; namely, 11% and 7% larger in diameter for 0.25%C and 5%C, respectively.

These results suggest higher water content of the 5%T microspheres, as compared to the ones prepared with 15%T.

Further, uniform microspheres were also fabricated consistently with varying Bis contents, yet exhibiting different morphologies. As shown in FIG. 1c, low Bis content (0.25%C) led to a high degree of swelling of the microspheres, with the degree of swelling decreasing with increasing Bis content up to 5%C (i.e., 12% and 8% decrease in diameter for 5%T and 15%T, respectively). While further increase in the Bis content (>10%C, rightmost column in FIG. 1c) having minimal impact on the swelling, the high Bis contents led to opaque or dark color for the microspheres. This opacity of the microspheres could be attributed to the formation of large pores rising from bundled polymer chains similar to the previously reported results from bulk PAAm gels prepared with such high Bis contents. See Righetti et al., *J. Biochem. Bioph. Methods,* 1981, 4, 347-363. Meanwhile, limitations of highly crosslinked microspheres arose from hydrophobicity of the crosslinker Bis (i.e., hydrophobic microspheres), such as nonspecific binding and false signal in fluorescence-based biosensing.

Moreover, addition of a small amount of LC PEG porogen (8 kDa) also yielded uniform microspheres without apparent compromise in the uniformity. See FIG. 1d. While increasing opacity of the microspheres similar to the high %C microspheres was observed, it indicated the formation of large pores. The larger pore formation with the PEG porogen could be attributed to phase separation between PEG and PAAm during polymerization that led to bundled PAAm chains (i.e., lateral aggregation). Remaining PEG porogens upon polymerization could be dissolved in water due to their hydrophilic nature, and the flexible linear PEG chains could readily diffuse out of crosslinked polymer networks while leaving large pores during washing steps. Note that multiple washing steps with 2-propanol and surfactant-containing aqueous solutions (Materials and Methods) would lead to disruption of weak non-covalent interactions between PEG chain and PAAm network, and thus complete removal of the PEG porogens from the PAAm microspheres. Meanwhile, since the phase separation-based method for the formation of large pores did not require high Bis content, the resulting microspheres would be hydrophilic thus offering a more suitable environment for efficient protein conjugation and biosensing with minimal nonspecific or hydrophobic adsorption.

As shown in FIGS. 1b-1d, the micromolding-based method enabled facile fabrication of highly uniform and well-defined PAAm-based microspheres for a wide range of prepolymer compositions. Importantly, this may not be readily achieved with photolithographic- or photopatterning-based methods owing to the slow polymerization rate of acrylamide (i.e., roughly one order of magnitude smaller chain propagation rate constant ($k_p$) for acrylamide compared to those for acrylates). In other words, the slow polymerization rate could result in less controllable size and shape of microscale hydrogels, attributed to diffusion of growing polymer chains and radicals into monomer regions that are not illuminated with UV light. In addition, the size of microspheres could be readily fine-tuned via a simple change of the mold volume, solvent evaporation of prepolymer solutions along with varying designs of mold geometry or via different solidification approaches (e.g., sol-gel reaction and colloidal assembly) in the micromolding method. Mass production of the microspheres could be also readily achieved via parallelization of the fabrication process. Meanwhile, microparticles with even larger array of morphologies and traits could be readily produced by minor extension of the micromolding scheme (e.g., multicompartmental microparticles via sequential micromolding and complex 3D-shaped ones via simple tuning of the interfacial deformation).

Finally, opacity of the microspheres with increasing PEG contents was further evaluated by comparing brightness of the microspheres to that of backgrounds, as shown in FIG. 1e.

These results show that the opacity decreased with increasing the PEG porogen content in a sigmoidal manner up to 7.5 w/v %, suggesting controllable pore size of the microspheres with the PEG porogen (further discussed in FIGS. 4 and 5 below) in a reliable manner.

In sum, the results described above demonstrate that the simple micromolding-based fabrication method enables consistent fabrication of uniform CS—PAAm microspheres for a wide range of prepolymer compositions due to the convenience and robustness of batch processing.

EXAMPLE 2

Retained Chemical Reactivity and Stable Incorporation of Chitosan

Studies were performed to evaluate the hydrogel microspheres prepared in EXAMPLE 1 as follows.

Figure 2:
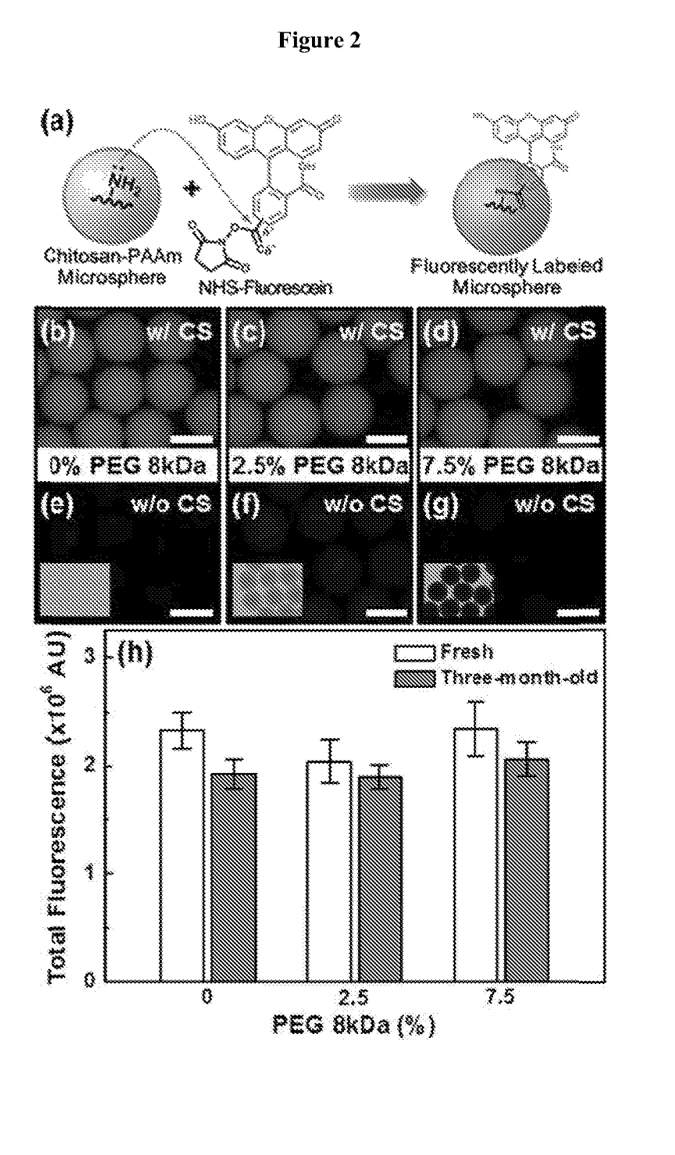

A simple fluorescent labeling reaction was conducted to examine the chemical reactivity of the CS—PAAm microspheres thus prepared and stable incorporation of the chitosan, as shown in FIGS. 2. 15%T and 5%C microspheres were fabricated with 0.5% chitosan and various contents of PEG porogen. The microspheres were then exposed to an N-hydroxysuccinimidyl ester form of carboxyfluorescein (NHS-fluorescein), which formed stable amide linkages with chitosan's primary amine groups via amidation reaction as shown in FIG. 2a. Of note, the chitosan's primary amines are highly reactive toward typical amine-reactive chemistries (e.g., using NHS ester, aldehyde, imidoester, epoxide etc.) under physiological conditions (i.e., neutral pH) due to their uniquely low $pK_a$ value (about 6.4), making chitosan a highly efficient conjugation handle for biofunctionalization.

The CS—PAAm microspheres prepared with a PEG porogen at various contents show bright fluorescence upon the fluorescent labeling reaction and thorough rinsing, indicating chemical reactivity of the microspheres toward amine-reactive chemistries. See FIGS. 2b-2d. Importantly, the fluorescent labeling results illustrate uniform fluorescence profile and equivalent fluorescence intensity upon 30 min reaction among the three PEG porogen conditions examined, suggesting ready access to chitosan's amine sites along with minimal mass transfer limitation of small fluorescein molecules (estimated diameter d being about 0.7 nm) through the microspheres. The uniform fluorescence across each microsphere area also suggests relatively uniform distribution of the chitosan moieties in the microspheres in contrast to reported results with CS-PEG, where most of the chitosan was incorporated around cores due to phase separation during polymerization. See Jung et al., *Chem. Mater.*, 2015, 27, 3988-3998. In the meantime, microspheres fabricated without chitosan (PAAm microspheres, FIGS. 2e-2g) exhibited negligible fluorescence for all the PEG porogen contents examined, confirming that the bright fluorescence on the CS—PAAm microspheres shown in FIGS. 2b-2d resulted from the specific reaction between chitosan's amine and NHS-fluorescein with minimal nonspecific binding of the fluorescein molecules. Note that the opaque microspheres (FIGS. 2f and 2g) did not show any nonspecific binding of fluorescein via hydrophobic interaction or scattering-based false fluorescence, suggesting potential of the CS—PAAm microspheres as a fluorescence-based biosensing platform upon biofunctionalization.

Stable incorporation of chitosan in the microspheres was also examined upon long term storage, by comparing total fluorescence intensity of freshly labeled CS—PAAm microspheres to that of the microspheres stored for three months in solution upon fluorescent labeling. See FIG. 2h. More specifically, average total fluorescence intensities of the 3 month-old CS—PAAm microspheres per each PEG porogen condition showed minimal decrease in the fluorescence (<18%), as compared to those of the freshly prepared ones. This result clearly illustrates that most of chitosan moieties were incorporated with the PAAm networks in a stable manner for long term storage. The stable incorporation of chitosan could be attributed to forming a covalent linkage between chitosan and acrylamide during free-radical polymerization. Meanwhile, minimal difference in the fluorescence intensity among the three different types of microspheres (<10%) illustrates that the PEG porogen did not significantly affect chitosan incorporation or its chemical reactivity.

On the whole, the fluorescent labeling results described above indicate that the CS—PAAm microspheres unexpectedly exhibited high chemical reactivity, minimal nonspecific binding of hydrophobic dyes, and chitosan stability upon long term storage.

EXAMPLE 3

Protein Conjugation Via Rapid Tetrazine-Trans-cyclooctene Ligation Reaction

Studies were performed to evaluate the protein conjugation of certain hydrogel microspheres as follows.

Figure 3:
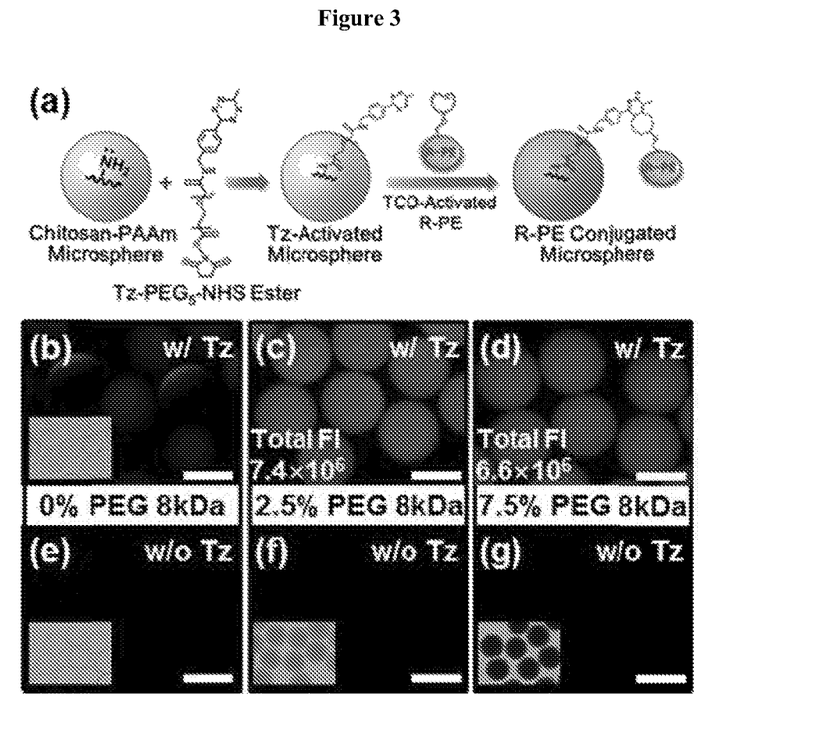
FIG. 3 is a schematic depiction of the effect of PEG porogen on protein conjugation with CS—PAAm microspheres. (a): A schematic diagram for R-phycoerythrin (R-PE) conjugation with microspheres via tetrazine-transcyclooctene (Tz-TCO) ligation reaction. (b)-(d): Fluorescence micrographs of microspheres prepared with various PEG porogen contents upon a conjugation reaction. (e)-(g): Fluorescence micrographs of microspheres missing Tz-activation upon incubation with TCO-modified R-Pes (each scale bar representing 200 μm), the insets being bright-field micrographs corresponding to their fluorescence micrographs.

FIG. 3 shows the effect of a PEG porogen on protein conjugation with the CS—PAAm microspheres using a bright red fluorescent protein R-phycoerythrin (R-PE, 240 kDa, hydrodynamic diameter $d_h$ being about 11.2 nm) via tetrazine-trans-cyclooctene (Tz-TCO) ligation reaction. R-PE is a suitable model protein for biosensing applications due to its size similar to antibodies (IgG, 150 kDa, $d_h$ being about 11 nm). On the other hand, Tz-TCO reaction offers high yields in a short reaction time and a bioorthogonal process for efficient biomolecular conjugation. See Karver et al., *Bioconjugate Chem.*, 2011, 22, 2263-2270. CS—PAAm microspheres containing chitosan moieties were prepared with the same compositions as shown in FIG. 2 (15%T & 5%C with various PEG porogen contents), in which the chitosan moieties were first activated with an NHS-ester form of Tz, and reacted with TCO-modified R-PEs for 24 h at room temperature as shown in FIG. 3a.

As shown in FIGS. 3b-3d, the Tz-activated CS—PAAm microspheres showed various degrees of fluorescence upon reaction with the TCO-modified R-PE's. More specifically, the microspheres prepared without PEG porogen exhibited minimal fluorescence (FIG. 3b), while those prepared with PEG porogen exhibited bright and uniform fluorescence (FIGS. 3c and 3d). In the meantime, the microspheres prepared with 7.5% PEG porogen show 11% lower fluorescence intensity, as compared to the ones prepared with 2.5% PEG (see FIG. 4, further discussed below). The minimal fluorescence of the microspheres prepared without PEG porogen could be attributed to limited diffusion of the large R-PEs ($d_h$ being about 11.2 nm), as compared to much smaller mesh size of the microspheres; reported mesh size of bulk PAAm gels prepared with 15%T and 5%C composition was about 2-3 nm. See Righetti et al., *Electrophoresis*, 1992, 13, 587-595. By contrast, the bright fluorescence on the microspheres prepared with PEG porogen clearly illustrates unexpected improvement in R-PE conjugation, suggesting the presence of large pores in the microspheres due to PEG porogen that allows for penetration of the R-PEs through the microspheres (see FIGS. 4 and 5, further discussed below).

Meanwhile, FIGS. 3e-3g show that the CS—PAAm microspheres without Tz activation exhibited negligible fluorescence at all tested conditions, clearly indicating the specific nature of the Tz-TCO ligation reaction and minimal nonspecific binding of the R-PEs with the CS—PAAm microspheres. These also show that the apparent protein loading capacity of the PAAm-based microspheres via hydrogen bonding was not significant, as compared to that by covalent bonding via the specific chemical reaction (FIGS. 3b-3d). In other words, the results shown in FIG. 3 demonstrate that the PAAm-based microsphere platforms have a substantially low-fouling nature.

In sum, the R-PE conjugation results described above indicate that the CS—PAAm microspheres prepared with low contents of PEG porogen unexpectedly exhibited improvement in protein conjugation, as well as non-fouling property.

EXAMPLE 4

Protein Conjugation Kinetics Behavior

Studies were performed to evaluate the protein conjugation kinetics behavior of certain hydrogel microspheres as follows.

Figure 4:
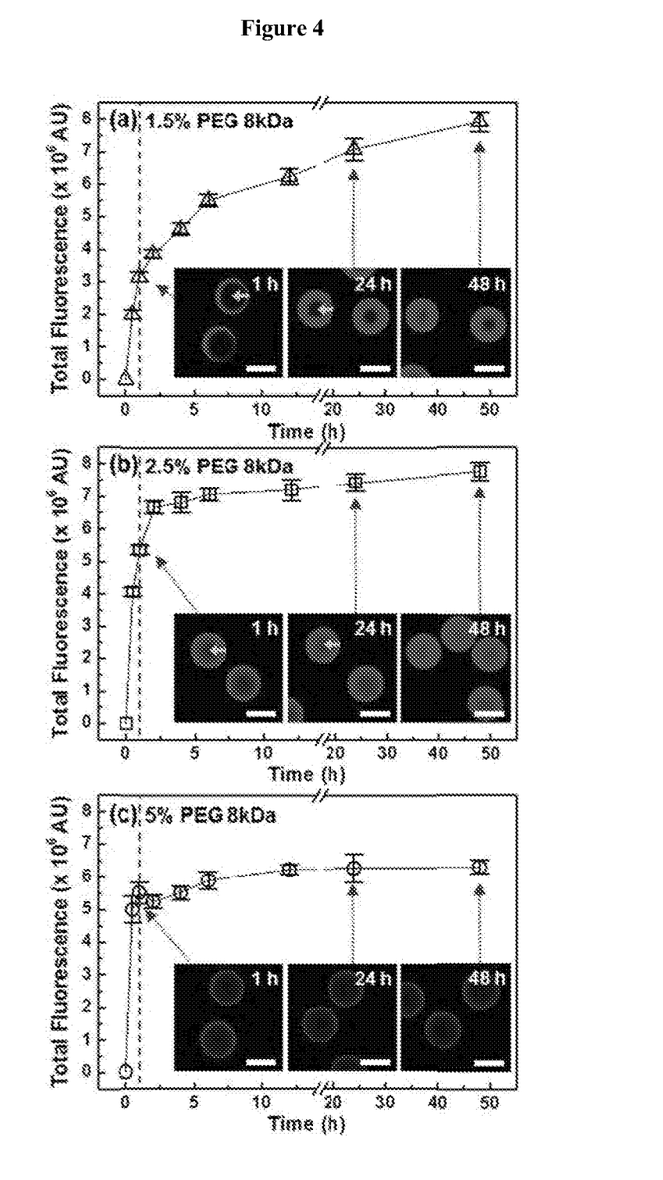
Figure 5:
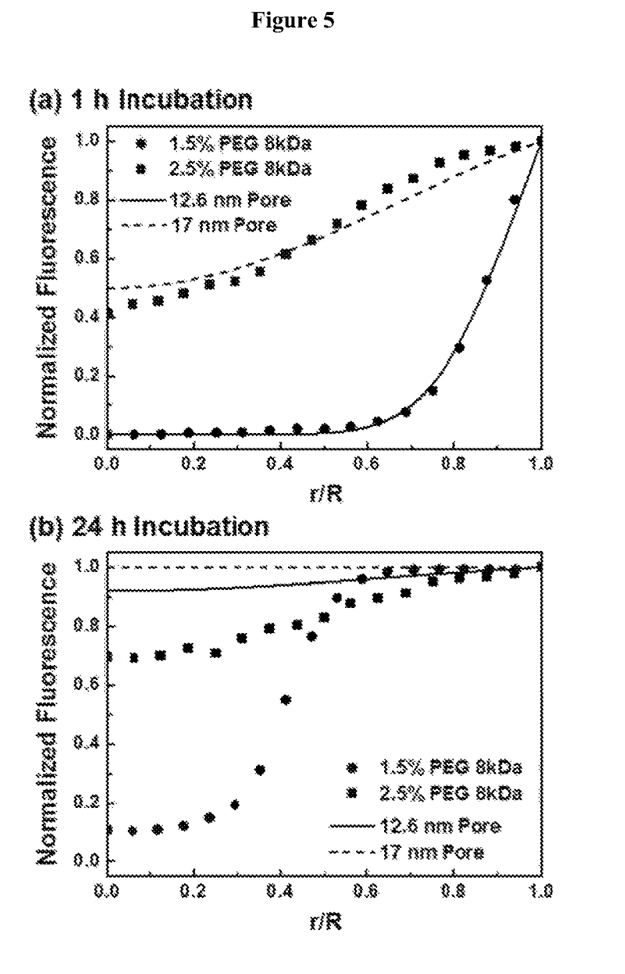

A thorough kinetic study was performed on the protein conjugation with the CS—PAAm microspheres prepared with PEG porogen as shown in FIG. 4. CS—PAAm microspheres were fabricated with various PEG contents and activated with Tz, then reacted with 2 μM of TCO-modified R-PEs for varying incubation times. The conjugation kinetics was then examined with confocal microscopy as well as total fluorescence intensity measured from epifluorescence micrographs.

FIG. 4a shows that the total fluorescence intensity plot of the CS—PAAm microspheres prepared with 1.5% PEG exhibited gradual increase in fluorescence with time during 48 h reaction period. More specifically, 40% of total fluorescence intensity at 48 h was reached upon 1 h conjugation reaction (dashed line) and 90% was reached upon 24 h, illustrating gradual conjugation of the R-PEs. Meanwhile, small error bars for each condition reveal consistency and robustness of our fabrication-conjugation approach. Further, confocal micrographs taken at the center plane of the microspheres also illustrate that the R-PEs progressively penetrated into the microspheres over time. These results clearly indicate the effect of PEG porogen on the pore formation allowing for penetration and conjugation of the R-PEs. Yet, the conjugation appeared to occur rapidly within the first few hours and then slow down. The slow protein conjugation could be attributed to hindered diffusion of the R-PEs through the microspheres whose pore size being similar to the size of the R-PE (see FIG. 5, further discussed below).

FIG. 4b shows that the microspheres prepared with 2.5% PEG exhibited considerable improvement in the apparent R-PE conjugation kinetics. More specifically, the total fluorescence reached 70% of the near-complete reaction level (i.e., total fluorescence intensity at 48 h) within the first hour of reaction (dashed line), suggesting rapid diffusion and conjugation of the R-PEs. The total fluorescence reached upon 48 h incubation was also equivalent to that with the 1.5% PEG porogen, suggesting minimal decrease in the conjugation capacity or accessibility upon addition of a higher PEG porogen content. Further, the confocal micrographs shown in FIG. 4b also supported this result, showing more rapid penetration than with the 1.5% PEG porogen throughout the 48 h reaction period and near-complete penetration and conjugation at the end of the 48 h reaction period. This improvement in protein conjugation kinetics indicates less hindered protein diffusion through the microspheres with the 2.5% PEG porogen condition than with the 1.5% PEG one, suggesting enlarged pores for the microspheres prepared with higher PEG porogen content. Meanwhile, the R-PE conjugation kinetics appeared to slow down upon reaching about 80% of the near-complete conjugation (i.e., upon 2 h reaction). This slowdown in the conjugation kinetics could be attributed to different pore sizes at the core and near the surface of the microspheres, suggesting smaller pore size at the core region (see FIG. 5, further discussed below).

The apparent protein conjugation kinetics was next examined with the microspheres prepared having relatively high content of PEG porogen (e.g., 5% and 7.5%). FIG. 4c shows the total fluorescence intensity plot and the confocal micrographs of the microspheres prepared with 5% PEG, representative of the conjugation kinetics results for the high PEG content range. The total fluorescence intensity plot in FIG. 4c shows more rapid increase in the total fluorescence than in the lower PEG porogen conditions shown in FIGS. 4a and 4b. More specifically, the total fluorescence reached approximately 80% of the maximum within the first hour of reaction (dashed line), and approached near-conjugation completion upon 6 h incubation (94% of total fluorescence intensity at 48 h). This result illustrates further improved R-PE conjugation kinetics with higher PEG porogen content.

In addition, FIG. 4c shows minimal difference in distribution of the conjugated R-PEs throughout the tested reaction periods, unlike low PEG porogen conditions, further supporting rapid R-PE penetration and conjugation. In the meantime, the maximum total fluorescence intensity of the microspheres prepared with 5% PEG was lower than in the low PEG porogen content conditions (1.5% and 2.5% PEG porogen, FIGS. 4a and 4b), and their corresponding confocal micrographs also exhibited less intense fluorescence under identical imaging conditions as shown in FIGS. 4a and 4b. This lower fluorescence could be attributed to anisotropically distributed and less accessible binding sites. More specifically, confocal micrographs of the fluorescein- and R-PE-conjugated microspheres prepared with 5% PEG porogen at various heights reveal that only the lower portions of the 5% PEG porogen microspheres were conjugated with either fluorescent marker, illustrating that the accessible binding sites exist primarily at the lower portions of the microspheres. Such anisotropic structure was also observed for the 2.5% PEG porogen microspheres to a less pronounced degree, suggesting that the PEG porogen may induce such phenomenon. Meanwhile, the controlled anisotropic structures observed in the microspheres suggest that the simple micromolding technique may provide a promising route to manufacture microspheres with a variety of asymmetric functionalities for biomedical applications such as therapeutic agent delivery, biosensing and bioimaging.

Importantly, the CS—PAAm microspheres prepared with 2.5% and 5% PEG porogen show much improvement in protein conjugation kinetics, as compared to that reported in Jung et al., Chem. Mater., 2015, 27, 3988-3998.

More specifically, CS-PEG microspheres with similar size to the CS—PAAm ones (about 200 μm in diameter) that were prepared with 10% and 20% PEGDA via the same micromolding-based method showed gradual increase in R-PE conjugation approaching conjugation completion during 48 h reaction period. By contrast, the CS—PAAm microspheres prepared with 2.5% and 5% PEG porogen yielded near-complete conjugation, i.e., about 90%, within 3 h and 1 h, respectively. This unexpected enhancement reveals less hindered mass transfer of the R-PEs through the CS—PAAm microspheres, suggesting the macroporous network structures that are attributed to bundled PAAm chains arising from phase separation between PEG porogens and growing PAAm networks during polymerization.

In conclusion, the protein conjugation kinetics results described above clearly indicate that addition of a low content of PEG porogen unexpectedly enabled formation of tunable and macroporous network structures leading to rapid protein penetration and conjugation, while higher PEG content conditions yielded anisotropic structures.

EXAMPLE 5

Analysis of R-PE Penetration and Pore Size

Studies were performed to evaluate R-PE penetration and pore sizes of certain hydrogel microspheres as follows.

Analysis of the R-PE penetration (i.e., mass transfer) of the microspheres was carried out to examine pore sizes and network structures of the hydrogel microspheres. Diffusion coefficients of the R-PE in the microspheres were calculated for various pore sizes ($D_m$) by utilizing Stokes-Einstein and Renkin equations, which describe diffusion coefficients of solutes (i.e., R-PE) in bulk solution and the relation between pore size and diffusion of the solutes in network structures, respectively, i.e., Equations 1 and 2 in Materials and Methods described above. Based on these diffusion coefficients, diffusion profiles (i.e., concentration distributions) of the R-PE in the microspheres were estimated using a non-steady state diffusion equation in a sphere, i.e., Equation 3. These profiles were then directly compared with normalized fluorescence profiles measured along the small arrows in the confocal micrographs of FIGS. 4a and 4b, which represent concentration distributions of the conjugated R-PE throughout the microspheres. Note that, while the R-PE conjugation with the microspheres is a diffusion-reaction coupled mass transfer system (i.e., R-PE diffusion through polymer networks and Tz-TCO reaction), the very rapid reaction rate of the Tz-TCO reaction ($k=820$ $M^{-1}S^{-1}$) would allow the conjugation to occur even at low concentration conditions, enabling the observed fluorescence resulting from the R-PE conjugation to represent R-PE's diffusion.

As shown in FIG. 5a, the normalized fluorescence profile plots over the microsphere radius (r/R) exhibited concentration distributions of the conjugated R-PE upon 1 h incubation for microspheres with 1.5% (solid circle) and 2.5% (solid square) PEG porogen. The estimated concentration distributions of the R-PE in microspheres with 12.6 nm ($D_m=4.87\times10^{-1}$ $cm^2s^{-1}$, solid line) and 17 nm ($D_m=4.96\times10^{-9}$ $cm^2s^{-1}$, dashed line) of pore sizes correlated well with the measured ones for microspheres with 1.5% and 2.5% PEG porogen, respectively.

This correlation suggests that effective pore sizes of the microspheres prepared with 1.5% and 2.5% PEG were 12.6 nm and 17 nm, respectively. Considering narrowed diffusion paths by the as-conjugated R-PEs ($d_h$ being about 11.2 nm), the actual pore sizes of the microspheres would be roughly 35 nm and 39 nm for the microspheres with 1.5% and 2.5% PEG, respectively.

FIG. 5b shows that the measured concentration distribution of the R-PE upon 24 h incubation for the microsphere with 1.5% PEG significantly deviated from the estimated one for 12.6 nm pore, unlike 1 h incubation, indicating much delayed mass transfer of the R-PE around the core region of the microsphere (0<r/R<0.5), as compared to the estimated result of near-complete penetration. This delayed mass transfer at long incubation time could be attributed to a core-shell like network structure of the microspheres, where the pore size around the core region was smaller than that near the sphere surface, leading to slowdown in the mass transfer rate as the R-PEs penetrated into the core. Such delayed mass transfer was also observed in the microsphere with 2.5% PEG (deviation from the estimated result for 17 nm pore, FIG. 5b) but to a less pronounced degree compared to the micro sphere with 1.5% PEG, suggesting that a higher PEG porogen content may lead to a structure possessing gradually decreased pore sizes.

The results described above suggest that the microspheres prepared with PEG porogen shown in FIGS. 4a and 4b contained core-shell like structures possessing pores of 35-39 nm in diameter at the shell and pores of smaller sizes around the core.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A macroporous polymeric hydrogel microsphere comprising chitosan and polyacrylamide, the chitosan being uniformly incorporated in a matrix formed of the polyacrylamide, wherein the microsphere has a diameter of 50-250 μm and an average pore size of 1-60 nm.

2. The hydrogel microsphere of claim 1, wherein the microsphere has a diameter of 150 μm to 250 μm and an average pore size of 10 nm to 60 nm.

3. The hydrogel microsphere of claim 2, wherein the microsphere has a diameter of 200-240 μm and an average pore size of 30-60 nm.

4. The hydrogel microsphere of claim 1, wherein the chitosan has an average molar mass of 100,000-1,000,000 Da.

5. The hydrogel microsphere of claim 1, wherein the chitosan has an average molar mass of 4,000-6,000 Da.

6. The hydrogel microsphere of claim 5, wherein the microsphere has a diameter of 200-240 μm and an average pore size of 30-60 nm.

7. The hydrogel microsphere of claim 1, wherein the microsphere is conjugatable to a biomolecule that has a molecular weight of 10,000-300,000 Da.

8. The hydrogel microsphere of claim 7, wherein the biomolecule has a molecular weight of 20,000 Da to 300,000 Da.

9. The hydrogel microsphere of claim 6, wherein the microsphere is conjugatable to a biomolecule that has a molecular weight of 10,000-300,000 Da.

10. The hydrogel microsphere of claim 9, wherein the biomolecule has a molecular weight greater than 20,000 Da.

11. The hydrogel microsphere of claim 1, wherein the hydrogel microsphere has an anisotropic network structure.

12. The hydrogel microsphere of claim 2, wherein the chitosan has an average molar mass of 100,000-1,000,000 Da.

13. The hydrogel microsphere of claim 3, wherein the chitosan has an average molar mass of 100,000-1,000,000 Da.

14. The hydrogel microsphere of claim 2, wherein the hydrogel microsphere has an anisotropic network structure.

15. The hydrogel microsphere of claim 3, wherein the hydrogel microsphere has an anisotropic network structure.

16. The hydrogel microsphere of claim 12, wherein the hydrogel microsphere has an anisotropic network structure.

17. The hydrogel microsphere of claim 13, wherein the hydrogel microsphere has an anisotropic network structure.

* * * * *